US010123760B2

(12) United States Patent
Hofmann (10) Patent No.: US 10,123,760 B2
(45) Date of Patent: Nov. 13, 2018

(54) METHOD AND SYSTEM FOR THE RECONSTRUCTION OF PLANNING IMAGES

(71) Applicant: Siemens Healthcare GmbH, Erlangen (DE)

(72) Inventor: Christian Hofmann, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 26 days.

(21) Appl. No.: 15/219,364

(22) Filed: Jul. 26, 2016

(65) Prior Publication Data

US 2017/0046832 A1 Feb. 16, 2017

(30) Foreign Application Priority Data

Aug. 14, 2015 (DE) .................. 10 2015 215 584

(51) Int. Cl.
*G06K 9/00* (2006.01)
*A61B 6/00* (2006.01)
(Continued)

(52) U.S. Cl.
CPC ............ *A61B 6/5205* (2013.01); *A61B 5/113* (2013.01); *A61B 6/032* (2013.01); *A61B 6/5288* (2013.01);
(Continued)

(58) Field of Classification Search
None
See application file for complete search history.

(56) References Cited

U.S. PATENT DOCUMENTS 6,580,938 B1 *  6/2003  Acker ................... A61B 5/415
                                                         600/424
8,873,819 B2 * 10/2014  Liu ....................... G06T 11/005
                                                         382/128
(Continued)

OTHER PUBLICATIONS

Ford, E. C., Mageras, G. S., Yorke, E., & Ling, C. C. (2003). Respiration-correlated spiral CT: A method of measuring respiratory-induced anatomic motion for radiation treatment planning. Medical physics, 30(1), 88-97.*

(Continued)

*Primary Examiner* — Vu Le
*Assistant Examiner* — Samah Beg
(74) *Attorney, Agent, or Firm* — Harness, Dickey & Pierce, P.L.C.

(57) ABSTRACT

A method for the reconstruction of planning images is based on a plurality of first respiratory cycles of a patient and tomographic raw data recorded at the same time as the first respiratory cycles being received. A reference cycle is determined based on respiratory cycles of the patient, in particular based on the first respiratory cycles of the patient. A reference cycle is subdivided into temporally equidistant reference phases, a reference amplitude being associated with each reference phase. The reference amplitudes are not equidistantly scanned therefore. Furthermore, the first respiratory cycles of the patient are subdivided into first phases, the temporal positions of the first phases each being based on one of the reference amplitudes. Reconstruction of planning images based on first intervals of the raw data follows, wherein the first intervals correspond to the first phases.

23 Claims, 3 Drawing Sheets

(51) Int. Cl.
*A61B 6/03* (2006.01)
*A61B 5/113* (2006.01)
*G06T 11/00* (2006.01)

(52) U.S. Cl.
CPC ........... *G06T 11/005* (2013.01); *A61B 6/5264* (2013.01); *G06T 2211/412* (2013.01)

(56) References Cited

U.S. PATENT DOCUMENTS

| | | | | |
|---|---|---|---|---|
| 9,795,355 | B2* | 10/2017 | Hofmann | A61B 6/5288 |
| 2004/0006375 | A1* | 1/2004 | Poezevera | A61N 1/3601 |
| | | | | 607/17 |
| 2007/0125378 | A1* | 6/2007 | Heinonen | A61B 5/0836 |
| | | | | 128/204.23 |
| 2009/0022379 | A1* | 1/2009 | Tashiro | A61B 6/466 |
| | | | | 382/131 |
| 2009/0187112 | A1* | 7/2009 | Meir | A61B 5/113 |
| | | | | 600/534 |
| 2009/0225957 | A1* | 9/2009 | Varchena | A61B 6/583 |
| | | | | 378/207 |
| 2011/0054339 | A1* | 3/2011 | Gass | A61B 7/04 |
| | | | | 600/529 |
| 2012/0245453 | A1* | 9/2012 | Tryggestad | A61B 6/463 |
| | | | | 600/413 |
| 2013/0266202 | A1* | 10/2013 | Yamada | A61B 6/032 |
| | | | | 382/131 |
| 2013/0274539 | A1* | 10/2013 | Yamada | A61N 5/1039 |
| | | | | 600/1 |
| 2013/0281805 | A1* | 10/2013 | Mason | A61B 5/0205 |
| | | | | 600/324 |
| 2014/0079304 | A1* | 3/2014 | Foo | G06T 11/008 |
| | | | | 382/131 |
| 2014/0133717 | A1* | 5/2014 | Kabus | A61B 6/5264 |
| | | | | 382/128 |
| 2014/0343345 | A1* | 11/2014 | Wu | A61N 5/1037 |
| | | | | 600/1 |
| 2015/0034083 | A1* | 2/2015 | Lellouche | G06K 9/00496 |
| | | | | 128/202.22 |
| 2015/0051480 | A1* | 2/2015 | Hwang | A61B 19/5244 |
| | | | | 600/424 |
| 2015/0310625 | A1* | 10/2015 | Shimamura | A61B 6/4233 |
| | | | | 382/132 |
| 2016/0113614 | A1* | 4/2016 | Cetingul | G06T 11/006 |
| | | | | 382/131 |
| 2016/0175614 | A1* | 6/2016 | Taguchi | A61N 5/1049 |
| | | | | 382/131 |
| 2016/0296193 | A1* | 10/2016 | Hofmann | A61B 6/03 |
| 2017/0076449 | A1* | 3/2017 | Chow | G06T 7/0012 |
| 2017/0091929 | A1* | 3/2017 | Hofmann | G06T 7/0012 |
| 2017/0172534 | A1* | 6/2017 | Shieh | A61B 6/5258 |
| 2017/0203123 | A1* | 7/2017 | Requardt | G06T 7/97 |
| 2017/0238895 | A1* | 8/2017 | Hofmann | A61B 5/0816 |
| 2017/0249740 | A1* | 8/2017 | Brehm | G06T 7/0026 |
| 2017/0294035 | A1* | 10/2017 | Hofmann | G06K 9/6202 |
| 2017/0328970 | A1* | 11/2017 | Bi | G01R 33/4818 |
| 2017/0332939 | A1* | 11/2017 | Subashi | A61B 5/055 |

OTHER PUBLICATIONS

Low, D. A., Nystrom, M., Kalinin, E., Parikh, P., Dempsey, J. F., Bradley, J. D., . . . & Politte, D. G. (2003). A method for the reconstruction of four-dimensional synchronized CT scans acquired during free breathing. Medical physics, 30(6), 1254-1263.*

Nehmeh, S. A., Erdi, Y. E., Pan, T., Yorke, E., Mageras, G. S., Rosenzweig, K. E., . . . & Larson, S. M. (2004). Quantitation of respiratory motion during 4D-PET/CT acquisition. Medical physics, 31 (6), 1333-1338.*

Pan, T., Lee, T. Y., Rietzel, E., & Chen, G. T. (2004). 4D-CT imaging of a volume influenced by respiratory motion on multislice CT. Medical physics, 31(2), 333-340.*

* cited by examiner

METHOD AND SYSTEM FOR THE RECONSTRUCTION OF PLANNING IMAGES

PRIORITY STATEMENT

The present application hereby claims priority under 35 U.S.C. § 119 to German patent application number DE 102015215584.6 filed Aug. 14, 2015, the entire contents of which are hereby incorporated herein by reference.

FIELD

At least one embodiment of the invention generally relates to a method and/or a system for the reconstruction of planning images.

BACKGROUND

Radiotherapy using high-energy X-ray radiation, electrons, protons or heavy ions is regularly used in order to treat tumors. With this kind of radiotherapy a target volume inside a patient is irradiated, with the tumor being at least partially located in the target volume. The target volume should be defined as precisely as possible, so the desired effect of the radiotherapy is primarily achieved in the target volume.

It is customary to record tomographic planning data of the patient in advance of radiotherapy for the planning thereof and for defining the target volume. Raw data is typically recorded using a computer tomograph, with the planning data being reconstructed from the raw data. The planning data comprises a plurality of planning images. It is possible to derive from this planning data how the anatomy of the patient and the position of the tumor change due to the breathing of the patient. Since, as a rule, radiotherapy occurs continuously it is important to take into account the change in the anatomy due to the breathing of the patient when planning radiotherapy and defining the target volume.

In order to associate the change in the anatomy with the course of the respiratory cycle of the patient, the breathing of the patient is likewise recorded with the aid of a breathing surrogate during the tomographic scanning. A breathing surrogate is a scanning system which is configured to record the respiratory cycle of the patient. For example, a breathing surrogate can be implemented by a chest strap or by a transducer attached to the chest of the patient. A breathing surrogate can also be implemented by a device for measuring the temperature of the breath of the patient.

Various approaches exist for reconstructing the planning data and for correlating this planning data with the respiratory cycles. The correlation can occur, in particular, by way of a phase-based method and by way of an amplitude-based method. In a phase-based method the raw data is selected for the reconstruction such that the respiratory cycles of the patient are scanned in a temporally equidistant manner. The planning data is therefore reconstructed such that adjacent planning images each have the same interval. In an amplitude-based method the raw data is selected for the reconstruction such that the amplitudes of the respiratory cycles of the patient are scanned equidistantly. Adjacent planning images can then have different intervals from each other.

Phase-based methods are more susceptible to irregular breathing of the patient and therefore have a greater number of and more pronounced artifacts than amplitude-based methods. Phase-based methods are primarily susceptible to variable plateaus during exhalation and to variable maximum amplitudes during inhalation and to variable breathing rates. Temporally equidistant planning images are desirable for certain types of planning of radiotherapy, however. It is therefore an object of the present invention to compensate for the drawback of known phase-based methods compared to amplitude-based methods. In particular, a method for the correlation of planning data with respiratory cycles of the patient shall be disclosed which is less susceptible to irregular breathing of the patient.

SUMMARY

Embodiments are directed to a method, a system, a computer program product and a machine-readable medium.

Features, advantages or alternative embodiments mentioned in this connection are similarly to be transferred to the other claimed subject matters and vice versa. In other words, the concrete claims (which are directed, for example, towards a device) can also be developed with the features which are described or claimed in conjunction with a method. The corresponding functional features of the method are formed by appropriate concrete modules.

A method, in at least one embodiment, for the reconstruction of planning images is based on a plurality of first respiratory cycles of patient and tomographic raw data recorded at the same time as the first respiratory cycles being received. The inventors recognized that it is advantageous to determine a reference cycle based on respiratory cycles of the patient, in particular based on the first respiratory cycles of the patient. A reference cycle of this kind is subdivided into temporally equidistant reference phases, wherein a reference amplitude is associated with each reference phase. The reference amplitudes are not equidistantly scanned therefore. Furthermore, the first respiratory cycles of the patient are subdivided into first phases, wherein the temporal positions of the first phases are each based on one of the reference amplitudes. Reconstruction of planning images based on first intervals of the raw data follows, wherein the first intervals correspond to the first phases.

An embodiment of the invention also relates to a system for the reconstruction of planning images comprising an interface for acquiring a plurality of first respiratory cycles and an arithmetic unit having a processor. The system is designed to carry out embodiments of the above-described method in that the interface and the arithmetic unit are designed to carry out the corresponding method steps. The system can also comprise a tomograph, in particular a computer tomograph, for recording the tomographic raw data. The system can also comprise a breathing surrogate for recording the first respiratory cycles of the patient.

An embodiment of the invention also relates to a computer program product having a computer program and a machine-readable medium. A largely software-based implementation has the advantage that even previously used systems or arithmetic units can be easily upgraded by a software update in order to work inventively. In addition to the computer program a computer program product of this kind can optionally comprise additional components such as, for example, documentation and/or additional components also hardware components, such as, for example, hardware keys (dongles, etc.) for utilization of the software.

BRIEF DESCRIPTION OF THE DRAWINGS

The invention will be described and illustrated in more detail below with reference to the example embodiments illustrated in the figures, in which.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

A method, in at least one embodiment, for the reconstruction of planning images is based on a plurality of first respiratory cycles of patient and tomographic raw data recorded at the same time as the first respiratory cycles being received. The inventors recognized that it is advantageous to determine a reference cycle based on respiratory cycles of the patient, in particular based on the first respiratory cycles of the patient. A reference cycle of this kind is subdivided into temporally equidistant reference phases, wherein a reference amplitude is associated with each reference phase. The reference amplitudes are not equidistantly scanned therefore. Furthermore, the first respiratory cycles of the patient are subdivided into first phases, wherein the temporal positions of the first phases are each based on one of the reference amplitudes. Reconstruction of planning images based on first intervals of the raw data follows, wherein the first intervals correspond to the first phases.

Like the first phases the first intervals each have a temporal position. Since the first respiratory cycles and the raw data were recorded at the same time, the first intervals can be unambiguously associated with the first phases. The first intervals correspond to the first phases insofar as a first phase with an identical temporal position can be associated with each first interval. The temporal position of a first phase is based on a reference amplitude associated with the first phase. Since a first phase corresponds to each first interval, a reference amplitude can also be associated with each first interval.

A plurality of first intervals corresponding to a similar first phase can now be combined for the reconstruction of a planning image. First phases are similar, in particular, if they are based on the same reference amplitude or are associated with the same reference amplitude. N reference phases can be numbered therefore, with each reference phase having a number n=1, 2, . . . N, and with N being a natural number. Each reference amplitude can also be associated with a number n therefore. A number n can accordingly also be associated with the first phases and the first intervals. The first intervals which are associated with the same number n can now be combined in each case. It is then advantageous to reconstruct N planning images in total.

Reconstruction of a planning image in a specific first phase is therefore based on specific first intervals associated with a reference amplitude. As a result only those intervals which are associated with the same reference amplitude are used for the reconstruction of a planning image in a specific first phase. Unlike in the established phase-based methods this prevents intervals of the raw data which are associated with completely different amplitudes being used for the reconstruction of a planning image in a specific first phase.

The reconstruction according to the proposed method also has the advantages of the amplitude-based methods. Since the first respiratory cycles are subdivided into first phases based on the reference amplitudes, the first phases of the patient are largely temporally equidistant. As a result the intervals of the raw data are also largely temporally equidistant. Due to association with the reference amplitudes the temporal positions of the first phases, and therewith the temporal positions of the first intervals, are less dependent on the regularity of the breathing of the patient. In particular, the proposed reconstruction is less susceptible to variable respiratory rates.

According to a further embodiment of the proposed method the raw data is formed as raw data continuously recorded by a computer tomograph in spiral mode. The continuous recording of raw data means the intervals can be selected without being limited by the raw data. As a result the first intervals can be selected such that they match the first phases as precisely as possible.

According to a further embodiment of the proposed method, the reference cycle is determined by averaging the respiratory cycles, in particular the first respiratory cycles. Averaging the respiratory cycles comprises averaging the amplitudes of the respiratory cycles, in particular of the first respiratory cycles. Individual amplitudes can be averaged at a specific instant or within a fixed time frame. The instant or time frame can be determined on the basis of reference points of the respiratory cycles. For example, the reference point can be the maximum amplitude or the beginning of inhalation. Averaging individual amplitudes can comprise calculation of an arithmetic mean, a geometric mean, a harmonic mean, a quadratic mean or also a median.

According to a further embodiment of the proposed method the reference cycle is determined in that the respiratory cycles, in particular the first respiratory cycles, are oriented relative to each other in accordance with their maximum amplitudes. In this case the maximum amplitudes are also reference points. The maximum amplitudes can be oriented such that they are all associated with the same reference instant.

According to a further embodiment of the proposed method, the reference amplitudes are designed as values relative to the maximum amplitude of the reference cycle. In particular, the reference amplitudes can be designed as fractions or percentages of the maximum amplitude. This ensures that the first respiratory cycles of the patient can be unambiguously subdivided into first phases based on the reference amplitudes.

According to a further embodiment of the proposed method, the first phases and the first intervals each have identical time frames. The raw data of a first interval has been recorded within the time frame in each case therefore. The time frame for first phases, and therefore for all first intervals, is preferably the same. The reference phases can also have corresponding time frames.

According to a further embodiment of the proposed method, the first respiratory cycles of the patient are subdivided such that the temporal intervals between adjacent first phases correspond to at least the time frame. The temporal intervals can be given by the intervals of the temporal positions of the adjacent phases. This ensures that adjacent phases do not overlap. In further variants of the proposed method the temporal intervals between adjacent first phases correspond to at least twice, five times or ten times the time frame.

According to a further embodiment of the proposed method, the temporal positions of the first phases are each based on a relationship of amplitudes of the first respiratory cycles to reference amplitudes. In particular, the temporal positions of the first phases can each correspond to marked amplitudes of the first respiratory cycles, wherein the marked amplitudes match the reference amplitudes. The marked amplitudes can match the reference amplitudes within a margin of error. The margin of error can be smaller by at least one order of magnitude than the marked amplitude.

According to a further embodiment of the proposed method, a respiratory state is associated with at least some of the reference phases, wherein the respiratory state comprises inhalation and exhalation, and wherein the first respiratory cycles of the patient are subdivided into first phases on the basis of the respiratory state. If there should be two identical reference amplitudes, this embodiment ensures that a reference amplitude can nevertheless be unambiguously associated with the first phases because identical reference amplitudes cannot be expected within one respiratory state.

An embodiment of the invention also relates to a system for the reconstruction of planning images comprising an interface for acquiring a plurality of first respiratory cycles and an arithmetic unit having a processor. The system is designed to carry out embodiments of the above-described method in that the interface and the arithmetic unit are designed to carry out the corresponding method steps. The system can also comprise a tomograph, in particular a computer tomograph, for recording the tomographic raw data. The system can also comprise a breathing surrogate for recording the first respiratory cycles of the patient.

An embodiment of the invention also relates to a computer program product having a computer program and a machine-readable medium. A largely software-based implementation has the advantage that even previously used systems or arithmetic units can be easily upgraded by a software update in order to work inventively. In addition to the computer program a computer program product of this kind can optionally comprise additional components such as, for example, documentation and/or additional components also hardware components, such as, for example, hardware keys (dongles, etc.) for utilization of the software.

Figure 1:
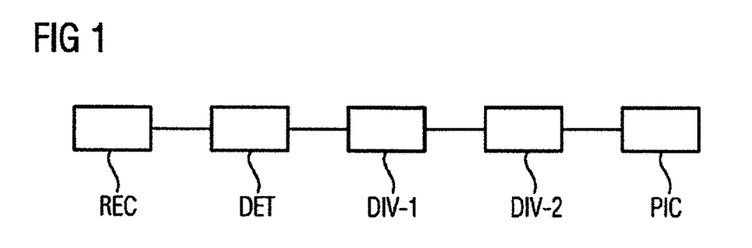
FIG. 1 shows a flowchart of a method for the reconstruction of planning images.

FIG. 1 shows a flowchart of a method for the reconstruction of planning images. A plurality of first respiratory cycles 18 of a patient 3 and of tomographic raw data 19 recorded at the same time as the first respiratory cycles 18 is received. An alternative embodiment of the invention also comprises the simultaneous recording of the first respiratory cycles 18 and the tomographic raw data 19. The respiratory cycles 19 can be recorded with a breathing surrogate 28. The tomographic raw data 19 can be recorded with a tomograph, in particular with a computer tomograph 1. The raw data 19 can then also be recorded continuously by a computer tomograph 1 in spiral mode.

Figure 2:
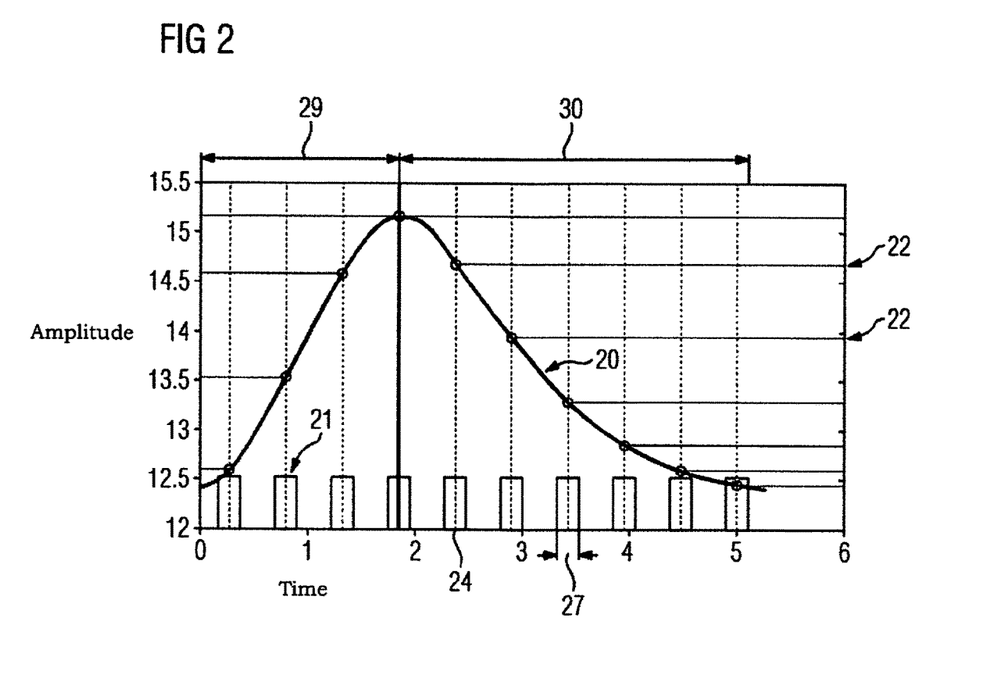
FIG. 2 shows a reference cycle having reference phases.

A reference cycle 20 is also determined based on respiratory cycles of the patient 3, in particular based on the first respiratory cycles 18. FIG. 2 shows a reference cycle 20 of this kind, with the amplitudes being plotted in arbitrary units on the vertical amplitudes axis against the time in seconds on the horizontal time axis. The reference amplitudes 22 and the associated temporal positions 24 are highlighted by whorls in FIG. 2. The reference amplitudes 22 are highlighted by horizontal solid lines and the associated temporal positions 24 are highlighted by vertical broken lines. The reference phases 21 are shown as bars. The height of these bars is arbitrarily chosen and is only for the purpose of illustration. The reference cycle 20 is determined by the first respiratory cycles 18 being oriented relative to each other according to their maximum amplitudes. Firstly therefore the maximum amplitudes are determined for each of the first respiratory cycles 18, and then the first respiratory cycles 18 are oriented relative to each other such that the maximum amplitudes have the same position along the time axis shown horizontally here. The maximum amplitudes can be determined manually as well as automatically using current methods of data processing. For example, the maximum amplitudes can be determined using a gradient method.

In the example shown here the reference cycle 20 has also been determined by averaging the first respiratory cycles 18. The amplitudes of the first respiratory cycles 18 overlaid on each other are averaged. Time frames, for example of 100 milliseconds or less, can be specified within which the amplitudes of the first respiratory cycles 18 overlaid on each other are averaged. In the example shown here the amplitudes are averaged by straightforward averaging.

The reference cycle 20 is also subdivided into temporally equidistant reference phases 21, wherein a reference amplitude 22 is associated with each reference phase 21. A reference phase 21 has at least one temporal position. As in the example shown in FIG. 2, a reference phase 21 can also have a time frame 27, with the temporal position 24 of a specific reference phase 21 lying within the time frame 27 of the specific reference phase 21. In different embodiments of the invention either the temporal intervals of the reference phases 21 and/or the number of reference phases 21 can be specified. In the example shown here the number of N=10 reference phases 21 is specified. Furthermore, the reference cycle 20 has been subdivided based on the maximum reference amplitude. A reference phase 21 has therefore been defined at the temporal position 24 of the maximum reference amplitude. The reference cycle 20 has then been subdivided equidistantly into the remaining nine reference phases 21. The reference phases 21 are numbered with increasing temporal positions 24 of the reference phases 21.

Figure 3:
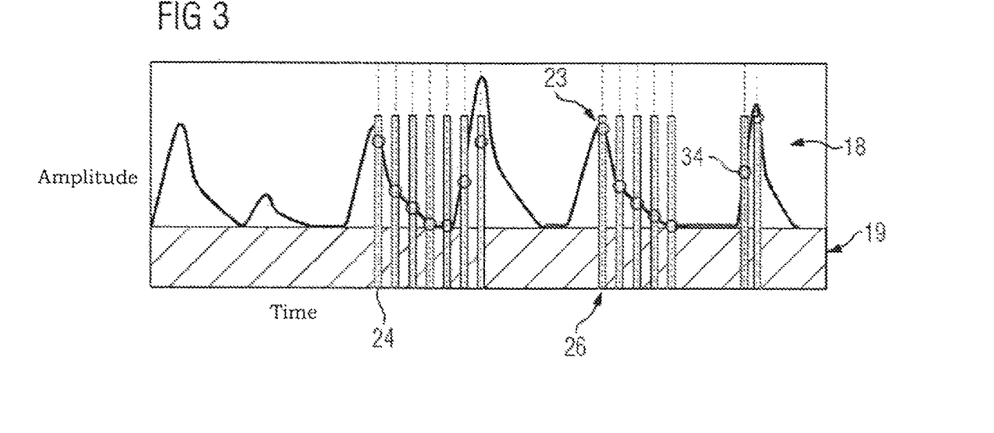
FIG. 3 shows first respiratory cycles having first phases and raw data having first intervals.

FIG. 3 shows first respiratory cycles 18 having first phases 23 and raw data 19 having first intervals 26. In the upper part of FIG. 3 the horizontal time axis indicates the temporal position 24 in arbitrary units. The vertical amplitudes axis indicates the amplitudes of the first respiratory cycles 18, and the horizontal time axis indicates the associated temporal position 24 in arbitrary units. The perpendicular broken lines highlight the temporal positions 24. The lower, hatched regions in FIG. 3 constitute the continuously recorded raw data 19. This raw data 19 is recorded at the same time as the first respiratory cycles 18. The first phases 23 correspond directly to the first intervals 26.

It can be seen that a reference amplitude 22 can be directly and unambiguously associated with each reference phase 21. The amplitudes and therewith the reference amplitudes 22 can be configured as values relative to the maximum amplitude of the reference cycle 22. These reference amplitudes 22 then allow the first respiratory cycles 18 to be subdivided into first phases 23 and the raw data 19 into first intervals 26. The temporal positions 24 of the first phases 23 are each based on a relationship of amplitudes 34 of the first respiratory cycles 18 to reference amplitudes 22. The relationship can consist in amplitudes 34 of the first respiratory cycles 18 matching the reference amplitudes 22, in particular within a specified margin of error. In the example shown here the amplitudes 34 are determined in the first respiratory cycles 18, which as far as possible exactly match the reference amplitudes 22. The first phases 23 are then associated with the temporal positions 24 of these specific amplitudes 34. The temporal positions 24 of the first phases 23 are thereby directly and unambiguously dependent on the reference amplitudes 22. The amplitudes 34 of the first phases 23 can also be called first amplitudes. The amplitudes 34 of the first phases 23 and the associated temporal positions 24 are highlighted by whorls in FIG. 3. The first phases 23 are shown as bars. The height of these bars is arbitrarily chosen and is used solely for the purpose of illustration.

In the example shown here the phases 23 have time frames 27 which are identical to the time frames 27 of the reference phases 21. In other embodiments of the invention the time frames 27 of the first phases 23 can be determined independently of the time frames 27 of the reference phases. The time frames 27 of the first phases 23 can all be identical or be different from each other. Furthermore, the first respiratory cycles 18 are subdivided into first phases 23 such that the time frames 27 of adjacent first phases 23 do not intersect. If the time frames 27 of the first phases 23 are identical then the temporal intervals between adjacent first phases 23 can correspond at least to the time frame 27. In further embodiments other minimum intervals can be specified between adjacent first phases 23. In particular, these minimum intervals can be given as absolute times, for example 500 milliseconds. The minimum interval of the first phases 23 can also match the temporal interval of the reference phases 21.

Furthermore, a respiratory state can be associated with each reference phase 21, with the respiratory state comprising inhalation 29 and exhalation 30. The respiratory state can be determined based on the maximum Amplitude in the reference cycle 20. The reference phases 21 can be associated with a temporal position 24, which is less than or equal to the temporal position 24 of the maximum amplitude, of inhalation 29. The reference phases 21 having a temporal position 24, which is greater than or equal to the temporal position 24 of the maximum amplitude, can be associated with exhalation 30. Since in the first respiratory cycles 18 a temporal position 24 is unambiguously associated with each amplitude and a maximum amplitude can be determined for each of the first respiratory cycles 18, a respiratory state can also be determined for each amplitude in the first respiratory cycles 18.

In the example shown in FIG. 2 the first three reference phases 21 are associated with inhalation 29, while the last six reference phases 21 are associated with exhalation 30. The fourth reference phase 21 can be associated with inhalation 29 and exhalation 30. The first respiratory cycles 18 can then be subdivided into first phases 23 based on the respiratory state. If, for example, two reference amplitudes 22 are very similar or identical, but are associated with different respiratory states, the respiratory state then acts as an additional feature for unambiguously identifying the respective reference amplitude 22. If an amplitude, which matches two identical reference amplitudes 22, has then been determined in a first respiratory cycle 18, a respiratory state can be associated with this amplitude. As a function of this respiratory state of the amplitude, this amplitude can then be associated with the reference phase 21 which has an identical respiratory state.

Furthermore, planning images based on first intervals 26 of the raw data 19 are reconstructed, with the first intervals 26 corresponding to the first phases 23. The first intervals 26 therefore correlate with the first phases 23. The first intervals 26 can therefore also be called raw data correlated with the first phases. FIG. 2 shows the correlation of the first phases 23 with the first intervals 26. The raw data 19 has been continuously recorded by a computer tomograph 1 in spiral mode. The first intervals 26 also have a time frame 27 which defines the temporal width of the first interval 26. If the first phase 23 has a time frame 27, then a first phase 23 having an identical time frame 27 can be associated with each first interval 26. Furthermore, the time frames 27 also define the temporal resolution of the planning images reconstructed from the first intervals 26. The shorter the time frame 27, and therewith the temporal width of the first intervals 26, is, the higher is the temporal resolution. The time frame 27 should, however, at least be so large that complete reconstruction of a planning image is possible. With a computer tomograph 1 a minimum time frame 27 of this kind corresponds to a recording range of 180°+a, where a is the opening angle of the X-ray fan beam or cone beam in the plane of rotation of the recording unit 17. The recording region refers here to a continuous rotation range of the recording unit 17.

During reconstruction a plurality of first intervals 26 corresponding to a similar first phase 23 is combined for the reconstruction of a planning image. Numbers from n=1, 2, ... N, where N=10 are associated with the first phases 23 and the corresponding first intervals 26. The number N corresponds to the number of reference phases 21. This ensures that only the raw data 19 which maps the target volume in similar breathing phases is combined for the reconstruction of a planning image. The proposed method therefore has fewer artifacts even in the case of irregular breathing of the patient 3. In particular, the proposed method has fewer artifacts in the case of an irregular respiratory rate of the patient 3.

Figure 4:
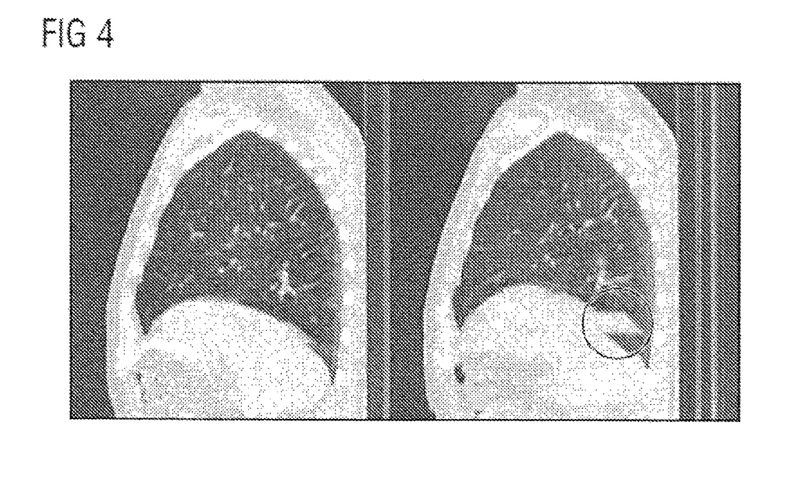
FIG. 4 shows a planning image as claimed in the proposed method and a planning image according to a conventional phase-based method.

The planning images can, in particular, be three-dimensional, 3D for short, images. The planning images can be configured as sectional images, as shown in FIG. 4, and as continuous volumes. The planning images can be reconstructed using conventional reconstruction algorithms, for example using a Feldkamp algorithm or by way of iterative reconstruction. The planning images are time-resolved insofar as they depict the target volume in a specific phase of the respiratory movement. The time resolution is determined by the temporal width of the time frames 27 of the first intervals 26. The planning data can comprise a moved depiction of the target volume, moreover, in that individual planning images are displayed according to the sequence defined by the reference phases 21. The sequence can be given, in particular, by the numbering n=1, 2, ... N.

FIG. 4 shows a planning image according to the proposed method and a planning image according to a conventional phase-based method. Both planning images are based on the same raw data 19 and show the torso of the patient 3 in a longitudinal section. A planning image according to the proposed method is displayed on the left-hand side of FIG. 4 while a planning image according to a conventional phase-based method is displayed on the right-hand side. In the planning image on the right-hand side an artifact can clearly be seen which is based on irregular breathing of the patient 3. The planning image on the left-hand side does not have an artifact of this kind.

Figure 5:
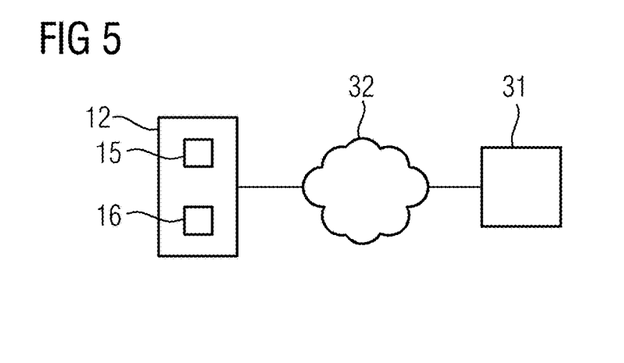
FIG. 5 shows a system for the reconstruction of planning images.

FIG. 5 shows a system for the reconstruction of planning images. In the simplest case the system comprises an interface 16 for receiving REC a plurality of first respiratory cycles 18 of a patient 3 and tomographic raw data 19 recorded at the same time as the first respiratory cycles 18, as well as an arithmetic unit 15 having a processor, wherein the processor is programmed to carry out at least the following steps:

determining DET a reference cycle 20 based on respiratory cycles of the patient 3, in particular based on the first respiratory cycles 18, first subdividing DIV-1 of the reference cycle 20 into temporally equidistant reference phases 21, wherein a reference amplitude 22 is associated with each reference phase 21, second subdividing DIV-2 of the first respiratory cycles 18 into first phases 23, wherein the temporal positions 24 of the first phases 23 are each based on a reference amplitude 22, reconstruction PIC of planning images based on first intervals 26 of the raw data 19, wherein the first intervals 26 correspond to the first phases 23.

The arithmetic unit 15 can also have a reconstruction unit 33 which is specifically designed to carry out the step of reconstruction PIC. The arithmetic unit 15 can also have a plurality of processors which are each programmed carry out individual steps of the proposed method. In further embodiments of the invention the processor can also be programmed to carry out the other method steps described above. Furthermore, the first respiratory cycles 18 and/or the raw data 19 can be stored on a server 23, so the first respiratory cycles 18 and/or the raw data 19 can be transmitted via a network 24 to a system for the reconstruction of planning images which is designed as a client. In the example shown here the client is implemented by the computer 12. An inventive computer program is then stored on client so as to be executable.

Figure 6:
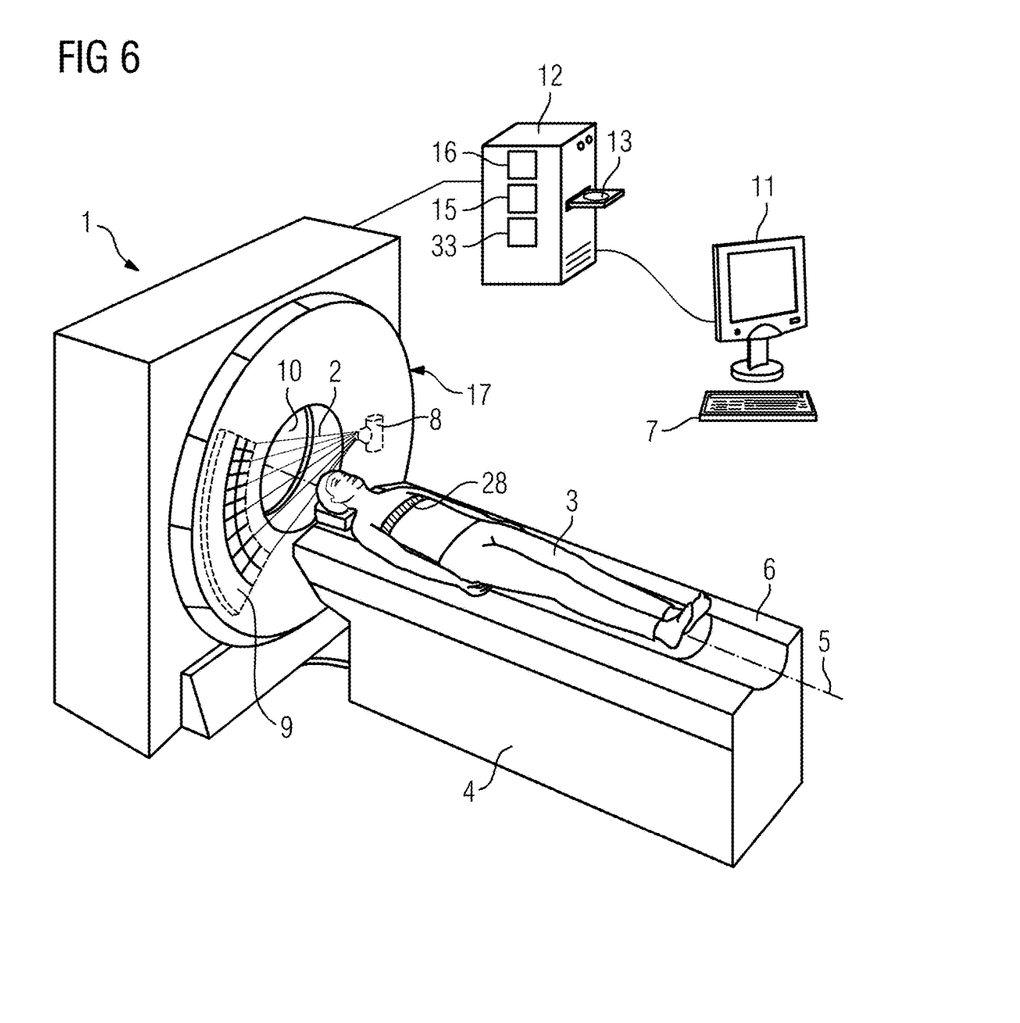
FIG. 6 shows a system for the reconstruction of planning images with a tomograph.

FIG. 6 shows a system for the reconstruction of planning images using a tomograph. The tomograph shown here is a computer tomograph 1. The computer tomograph 1 shown here has a recording unit 17, comprising a radiation source 8 in the form of an X-ray source and a radiation detector 9 in the form of an X-ray detector. During the recording of raw data 19 the recording unit 17 rotates about a system axis 5, and during recording the X-ray source emits rays 2 in the form of X-rays. In the example shown here the X-ray source is an X-ray tube. In the example shown here the X-ray detector is a line detector having a plurality of lines.

In the example shown here a patient 3 lies on an examination table 6 during recording of raw data 19. The examination table 6 is connected to a table base 4 such that it supports the examination table 6 with the patient 3. The examination table 6 is designed to move the patient 3 in a recording direction through the opening 10 in the recording unit 17. The recording direction is given, as a rule, by the system axis 5, about which the recording unit 17 rotates during recording of raw data 19. In the case of a spiral scan the examination table 6 is moved continuously through the opening 10 while the recording unit 17 rotates around the patient 3 and records raw data 19. The X-rays therefore describe a spiral on the surface of the patient 3.

The system shown here also has a breathing surrogate 28 in the form of a chest strap. The breathing surrogate 28 is designed to record respiratory cycles of the patient 3, in particular the first respiratory cycles 18, and to transmit them via an interface 16 on the computer 12. In the example shown here the interface 16 is designed as part of a computer 12. The interface 16 is a generally known hardware or software interface, e.g. the hardware interface PCI bus, USB or Firewire. The computer 12 is connected to an output unit in the form of a screen 11, and to an input unit 7. The screen 11 is designed for displaying various items of information, in particular the planning images. The input unit 7 can be used to start the inventive computer program or to select parameters for carrying out the inventive method. The input unit 7 is, for example, a keyboard, mouse, what is known as a touchscreen, or a microphone for speech input.

The computer 12 of the system shown here for the reconstruction of planning images also comprises a reconstruction unit 33. The system also has an arithmetic unit 15. The arithmetic unit 15 can cooperate with a machine-readable data carrier 13, in particular to carry out an inventive method by way of a computer program with program code. The computer program can also be stored on the machine-readable data carrier 13 so as to be retrievable. In particular, the machine-readable data carrier can be a CD, DVD, Blu-Ray disk, a memory stick or a hard disk. The arithmetic unit 15 and the reconstruction unit 33 can be designed in the form of hardware and/or in the form of software. For example, the reconstruction unit 33 can be designed as what is known as an FPGA (acronym for Field Programmable Gate Array) or comprise an arithmetic logic unit. The arithmetic unit 15 shown here has a processor. The processor can be designed as a microprocessor and have a plurality of cores.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for reconstructing planning images, comprising:
    receiving a plurality of respiratory cycles of a patient and tomographic raw data, the tomographic raw data being recorded contemporaneously with the plurality of respiratory cycles;
    determining a reference cycle based on the plurality of respiratory cycles;
    subdividing the reference cycle into a plurality of reference phases, the plurality of reference phases being temporally equidistant, each of the plurality of reference phases being associated with a respective reference amplitude of a plurality of reference amplitudes, each of the plurality of reference amplitudes having a respective amplitude value of a plurality of amplitude values;
    subdividing each of the plurality of respiratory cycles into a plurality of respiratory phases, each of the plurality of respiratory phases having a temporal position based on a different reference amplitude of the plurality of reference amplitudes; and
    reconstructing the planning images based on a plurality of intervals of the tomographic raw data, each of the plurality of intervals corresponding to a respective respiratory phase of the plurality of respiratory phases.

2. The method of claim 1, wherein the tomographic raw data is continuously recorded by a computer tomograph in spiral mode.

3. The method of claim 2, wherein the determining the reference cycle includes averaging the plurality of respiratory cycles.

4. The method of claim 1, wherein the determining the reference cycle includes averaging the plurality of respiratory cycles.

5. The method of claim 4, wherein the determining the reference cycle includes orienting the plurality of respiratory cycles relative to each other in accordance with maximum amplitudes of the plurality of respiratory cycles.

6. The method of claim 1, wherein the determining the reference cycle includes orienting the plurality of respiratory cycles relative to each other in accordance with maximum amplitudes of the plurality of respiratory cycles.

7. The method of claim 1, wherein the plurality of amplitude values are configured relative to a maximum amplitude of the reference cycle.

8. The method of claim 1, wherein each of the plurality of respiratory phases and each of the plurality of intervals have time frames, all of the time frames having the same length.

9. The method of claim 8, wherein the subdividing each of the plurality of respiratory cycles subdivides the plurality of respiratory cycles such that time intervals between adjacent respiratory phases of the plurality of respiratory phases correspond to the length of the time frames and such that none of the time frames overlap.

10. The method of claim 1, wherein the temporal positions of the plurality of respiratory phases are each based on a relationship of amplitudes of each respiratory cycle of the plurality of respiratory cycles to the plurality of amplitude values.

11. The method of claim 1, wherein a respiratory state is associated with one or more of the plurality of reference phases, the respiratory state being one of inhalation and exhalation, and the subdividing each of the plurality of respiratory being based on the respiratory state.

12. A system for reconstructing planning images comprising:
    an interface configured to receive a plurality of respiratory cycles of a patient and tomographic raw data, the tomographic raw data being recorded contemporaneously with the plurality of respiratory cycles;
    a memory configured to store a program; and
    at least one processor connected to the memory, the at least one processor being configured to execute the program to
        determine a reference cycle based on the plurality of respiratory cycles,
        subdivide the reference cycle into a plurality of reference phases, the plurality of reference phases being temporally equidistant, each of the reference phases of the plurality of reference phases being associated with a respective reference amplitude of a plurality of reference amplitudes, each of the plurality of reference amplitudes having a respective amplitude value of a plurality of amplitude values,
        subdivide each of the plurality of respiratory cycles into a plurality of respiratory phases, each of the plurality of respiratory phases having a temporal position based on a different reference amplitude of the plurality of reference amplitudes, and
        reconstruct the planning images based on a plurality of intervals of the tomographic raw data, each of the plurality of intervals corresponding to a respective respiratory phase of the plurality of respiratory phases.

13. The system of claim 12, further comprising:
a tomograph configured to record the tomographic raw data.

14. The system of claim 13, wherein the tomograph is a computer tomograph.

15. The system of claim 14, further comprising:
a breathing surrogate configured to record the plurality of respiratory cycles.

16. The system of claim 13, further comprising:
a breathing surrogate configured to record the plurality of respiratory cycles.

17. The system of claim 12, further comprising:
a breathing surrogate configured to record the plurality of respiratory cycles.

18. A memory of a system for reconstructing planning images, the memory storing a computer program that, when executed by at least one processor, causes the at least one processor to carry out the method of claim 1.

19. A non-transitory machine-readable medium storing a computer program that, when executed by at least one processor of a system for documenting a diagnostic test, causes the at least one processor to carry out the method of claim 1.

20. A memory of a system for reconstructing planning images, the memory storing a computer program that, when executed by at least one processor, causes the at least one processor to carry out the method of claim 2.

21. A non-transitory machine-readable medium storing a computer program that, when executed by at least one processor of a system for documenting a diagnostic test, causes the at least one processor to carry out the method of claim 2.

22. A memory of a system for reconstructing planning images, the memory storing a computer program that, when executed by at least one processor, causes the at least one processor to carry out the method of claim 4.

23. A non-transitory machine-readable medium storing a computer program that, when executed by at least one processor of a system for documenting a diagnostic test, causes the at least one processor to carry out the method of claim 4.

* * * * *